United States Patent
Wright et al.

(10) Patent No.: US 9,987,406 B2
(45) Date of Patent: Jun. 5, 2018

(54) MAGNETIC SENSORS AND RELATED SYSTEMS AND METHODS

(75) Inventors: Nigel Wright, California, PA (US); Gregory Jubic, Leechburg, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 765 days.

(21) Appl. No.: 13/984,087

(22) PCT Filed: Jan. 18, 2012

(86) PCT No.: PCT/US2012/021667
§ 371 (c)(1),
(2), (4) Date: Oct. 10, 2013

(87) PCT Pub. No.: WO2012/108984
PCT Pub. Date: Aug. 16, 2012

(65) Prior Publication Data
US 2014/0031736 A1    Jan. 30, 2014

Related U.S. Application Data

(60) Provisional application No. 61/440,519, filed on Feb. 8, 2011.

(51) Int. Cl.
*A61M 1/14*    (2006.01)
*A61M 1/34*    (2006.01)
(Continued)

(52) U.S. Cl.
CPC .............. *A61M 1/14* (2013.01); *A61M 1/342* (2013.01); *A61M 1/3458* (2014.02);
(Continued)

(58) Field of Classification Search
CPC ...... A61M 1/14; A61M 1/342; A61M 1/3458; A61M 1/3669; A61M 1/367; A61M 2205/3317; G01R 33/02
See application file for complete search history.

(56) References Cited

U.S. PATENT DOCUMENTS 3,605,741 A  *  9/1971  Spencer ............ A61M 5/16886
                                                        137/558
4,652,257 A  *  3/1987  Chang .................. A61K 9/1273
                                                        600/12
(Continued)

FOREIGN PATENT DOCUMENTS

EP    0146310    6/1985
EP    0426273    5/1991
(Continued)

OTHER PUBLICATIONS

Notification of Transmittal of the International Search Report and the Written Opinion of the International Searching Authority, dated Jul. 31, 2012, 17 pages.

*Primary Examiner* — Susan Su
*Assistant Examiner* — Kai Weng
(74) *Attorney, Agent, or Firm* — Fish & Richardson P.C.

(57) ABSTRACT

This invention relates generally to magnetic sensors and related systems and methods. In some aspects of the invention, a magnetic sensor assembly includes a housing configured to releasably hold a medical fluid tube and a sensor secured to the housing, the sensor configured to detect a change in a strength of a magnetic field when a medical fluid passes through the medical fluid tube.

8 Claims, 6 Drawing Sheets

(51) Int. Cl.
  *G01R 33/02* (2006.01)
  *A61M 1/36* (2006.01)
(52) U.S. Cl.
  CPC .......... *A61M 1/3462* (2013.01); *A61M 1/367* (2013.01); *G01R 33/02* (2013.01); *A61M 1/3669* (2013.01); *A61M 2205/3317* (2013.01); *A61M 2205/502* (2013.01)

(56) References Cited

U.S. PATENT DOCUMENTS

| | | |
|---|---|---|
| 4,775,369 A | 10/1988 | Schwartz |
| 4,898,578 A | 2/1990 | Rubalcaba |
| 4,915,688 A | 4/1990 | Bischof et al. |
| 4,925,444 A | 5/1990 | Orkin et al. |
| 4,943,279 A | 7/1990 | Samiotes et al. |
| 4,946,439 A | 8/1990 | Eggers |
| 4,959,050 A | 9/1990 | Bobo |
| 4,966,579 A | 10/1990 | Polaschegg |
| 4,981,467 A | 1/1991 | Bobo et al. |
| 5,037,390 A | 8/1991 | Raines et al. |
| 5,041,086 A | 8/1991 | Koenig et al. |
| 5,047,014 A | 9/1991 | Mosebach et al. |
| 5,049,129 A | 9/1991 | Zdeb et al. |
| 5,053,019 A | 10/1991 | Duffy |
| 5,057,076 A | 10/1991 | Polaschegg |
| 5,074,756 A | 12/1991 | Davis |
| 5,078,683 A | 1/1992 | Sancoff et al. |
| 5,102,392 A | 4/1992 | Sakai et al. |
| 5,122,123 A | 6/1992 | Vaillancourt |
| 5,122,129 A | 6/1992 | Olson et al. |
| 5,127,618 A | 7/1992 | Page et al. |
| 5,169,388 A | 12/1992 | McPhee |
| 5,176,631 A | 1/1993 | Koenig |
| 5,193,990 A | 3/1993 | Kamen et al. |
| 5,200,627 A | 4/1993 | Chevallet |
| 5,207,642 A | 5/1993 | Orkin et al. |
| 5,211,201 A | 5/1993 | Kamen et al. |
| 5,213,483 A | 5/1993 | Flaherty et al. |
| 5,246,347 A | 9/1993 | Davis |
| 5,252,044 A | 10/1993 | Raines et al. |
| 5,256,157 A | 10/1993 | Samiotes et al. |
| 5,304,126 A | 4/1994 | Epstein et al. |
| 5,304,165 A | 4/1994 | Haber et al. |
| 5,317,506 A | 5/1994 | Coutre et al. |
| 5,324,258 A | 6/1994 | Rohrbough |
| 5,329,976 A | 7/1994 | Haber et al. |
| 5,378,231 A | 1/1995 | Johnson et al. |
| 5,382,232 A | 1/1995 | Hague et al. |
| 5,392,638 A | 2/1995 | Kawahara |
| 5,401,237 A | 3/1995 | Tachibana et al. |
| 5,421,812 A | 6/1995 | Langley et al. |
| 5,431,626 A | 7/1995 | Bryant et al. |
| 5,431,627 A | 7/1995 | Pastrone et al. |
| 5,438,510 A | 8/1995 | Bryant et al. |
| 5,445,621 A | 8/1995 | Poli et al. |
| 5,464,392 A | 11/1995 | Epstein et al. |
| 5,494,822 A | 2/1996 | Sadri |
| 5,496,273 A | 3/1996 | Pastrone et al. |
| 5,531,697 A | 7/1996 | Olsen et al. |
| 5,531,698 A | 7/1996 | Olsen |
| 5,533,389 A | 7/1996 | Kamen et al. |
| 5,547,470 A | 8/1996 | Johnson et al. |
| 5,552,118 A | 9/1996 | Mayer |
| 5,573,502 A | 11/1996 | LeCocq et al. |
| 5,575,310 A | 11/1996 | Kamen et al. |
| 5,578,223 A | 11/1996 | Bene et al. |
| 5,609,575 A | 3/1997 | Larson et al. |
| 5,616,124 A | 4/1997 | Hague et al. |
| 5,641,892 A | 6/1997 | Larkins et al. |
| 5,643,218 A | 7/1997 | Lynn et al. |
| 5,651,775 A | 7/1997 | Walker et al. |
| 5,691,484 A | 11/1997 | Feller |
| 5,698,090 A | 12/1997 | Bene et al. |
| 5,713,865 A | 2/1998 | Manning et al. |
| 5,743,886 A | 4/1998 | Lynn et al. |
| 5,745,378 A | 4/1998 | Barker et al. |
| 5,752,931 A | 5/1998 | Nazarian et al. |
| 5,755,563 A | 5/1998 | Clegg et al. |
| 5,785,701 A | 7/1998 | Sams et al. |
| 5,800,387 A | 9/1998 | Duffy et al. |
| 5,816,779 A | 10/1998 | Lawless et al. |
| 5,843,035 A | 12/1998 | Bowman et al. |
| 5,855,782 A | 1/1999 | Falkenhagen et al. |
| 5,873,872 A | 2/1999 | Thibault et al. |
| 5,897,526 A | 4/1999 | Vaillancourt |
| 5,916,197 A | 6/1999 | Reilly et al. |
| 5,925,011 A | 7/1999 | Faict et al. |
| 5,935,099 A | 8/1999 | Peterson et al. |
| 5,935,105 A | 8/1999 | Manning et al. |
| 5,938,636 A | 8/1999 | Kramer et al. |
| 5,941,848 A | 8/1999 | Nishimoto et al. |
| 5,989,423 A | 11/1999 | Kamen et al. |
| 6,017,318 A | 1/2000 | Gauthier et al. |
| 6,019,750 A | 2/2000 | Fowles et al. |
| 6,041,801 A | 3/2000 | Gray et al. |
| 6,065,941 A | 5/2000 | Gray et al. |
| 6,068,612 A | 5/2000 | Bowman et al. |
| 6,070,761 A | 6/2000 | Bloom et al. |
| 6,077,246 A | 6/2000 | Kullas et al. |
| 6,099,492 A | 8/2000 | Le Boeuf |
| 6,110,153 A | 8/2000 | Davis et al. |
| 6,117,103 A | 9/2000 | Tverskoy et al. |
| 6,123,686 A | 9/2000 | Olsen et al. |
| 6,126,637 A | 10/2000 | Kriesel et al. |
| 6,142,008 A | 11/2000 | Cole et al. |
| 6,210,361 B1 | 4/2001 | Kamen et al. |
| 6,241,704 B1 | 6/2001 | Peterson et al. |
| 6,269,340 B1 | 7/2001 | Ford et al. |
| 6,299,131 B1 | 10/2001 | Ryan |
| 6,302,653 B1 | 10/2001 | Bryant et al. |
| 6,321,941 B1 | 11/2001 | Argentieri et al. |
| 6,464,667 B1 | 10/2002 | Kamen et al. |
| 6,468,242 B1 | 10/2002 | Wilson et al. |
| 6,471,872 B2 | 10/2002 | Kitaevich et al. |
| 6,475,180 B2 | 11/2002 | Peterson et al. |
| 6,489,896 B1 | 12/2002 | Platt et al. |
| 6,527,758 B2 | 3/2003 | Ko |
| 6,575,930 B1 | 6/2003 | Trombley et al. |
| 6,604,908 B1 | 8/2003 | Bryant et al. |
| 6,610,024 B1 | 8/2003 | Benatti |
| 6,616,633 B1 | 9/2003 | Butterfield et al. |
| 6,622,542 B2 | 9/2003 | Derek et al. |
| 6,658,396 B1 | 12/2003 | Tang et al. |
| 6,692,478 B1 | 2/2004 | Paradis |
| 6,695,803 B1 | 2/2004 | Robinson et al. |
| 6,699,230 B2 | 3/2004 | Jaafar et al. |
| 6,726,656 B2 | 4/2004 | Kamen et al. |
| 6,731,971 B2 | 5/2004 | Evans et al. |
| 6,736,972 B1 | 5/2004 | Matson |
| 6,780,322 B1 | 8/2004 | Bissler et al. |
| 6,802,892 B2 | 10/2004 | Newman et al. |
| 6,877,713 B1 | 4/2005 | Gray et al. |
| 6,985,870 B2 | 1/2006 | Martucci et al. |
| 6,986,759 B1 | 1/2006 | Jeremijevic |
| 7,029,456 B2 | 4/2006 | Ware et al. |
| 7,060,049 B2 | 6/2006 | Trombley et al. |
| 7,092,796 B2 | 8/2006 | Vanderveen |
| 7,107,837 B2 | 9/2006 | Lauman et al. |
| 7,128,105 B2 | 10/2006 | Tribble et al. |
| 7,150,735 B2 | 12/2006 | Hickle |
| 7,204,823 B2 | 4/2007 | Estes et al. |
| 7,214,210 B2 | 5/2007 | Kamen et al. |
| 7,326,186 B2 | 2/2008 | Trombley et al. |
| 7,338,470 B2 | 3/2008 | Katz et al. |
| 7,347,849 B2 | 3/2008 | Brugger et al. |
| 7,427,281 B2 | 9/2008 | Uber |
| 7,517,332 B2 | 4/2009 | Tonelli et al. |
| 7,559,524 B2 | 7/2009 | Gray et al. |
| 7,575,567 B2 | 8/2009 | Simpkins |
| 7,628,184 B2 | 12/2009 | Py et al. |
| 7,632,078 B2 | 12/2009 | Demers et al. |
| 7,641,626 B2 | 1/2010 | Tonelli et al. |
| 7,654,976 B2 | 2/2010 | Peterson et al. |

(56) References Cited

U.S. PATENT DOCUMENTS

| | | | |
|---|---|---|---|
| 7,661,293 B2 | 2/2010 | Dam | |
| 7,661,294 B2 | 2/2010 | Dam | |
| 7,662,139 B2 | 2/2010 | Demers et al. | |
| 7,668,731 B2 | 2/2010 | Martucci et al. | |
| 7,699,806 B2 | 4/2010 | Ware et al. | |
| 7,762,989 B2 | 7/2010 | Simpson | |
| 7,766,873 B2 | 8/2010 | Moberg et al. | |
| 7,837,647 B2 | 11/2010 | Estes et al. | |
| 7,837,651 B2 | 11/2010 | Bishop et al. | |
| 7,905,861 B2 | 3/2011 | Rhinehart et al. | |
| 7,922,708 B2 | 4/2011 | Estes et al. | |
| 7,967,783 B2 | 6/2011 | Rebours | |
| 7,967,785 B2 | 6/2011 | Morgan et al. | |
| 7,981,101 B2 | 7/2011 | Walsh | |
| 7,981,280 B2 | 7/2011 | Carr et al. | |
| 7,985,198 B2 | 7/2011 | von Blumenthal et al. | |
| 7,998,115 B2 | 8/2011 | Bedingfield | |
| 8,353,870 B2 | 1/2013 | Levin et al. | |
| 2002/0045571 A1 | 4/2002 | Liu et al. | |
| 2003/0153895 A1 | 8/2003 | Leinsing | |
| 2003/0191445 A1 | 10/2003 | Wallen et al. | |
| 2005/0085760 A1 | 4/2005 | Ware et al. | |
| 2005/0203329 A1 | 9/2005 | Muto et al. | |
| 2005/0209563 A1 | 9/2005 | Hopping et al. | |
| 2005/0230292 A1 | 10/2005 | Beden et al. | |
| 2006/0025747 A1 | 2/2006 | Sullivan et al. | |
| 2006/0084905 A1 | 4/2006 | Montgomery et al. | |
| 2006/0089594 A1 | 4/2006 | Landau | |
| 2006/0229557 A1 | 10/2006 | Fathallah et al. | |
| 2007/0156089 A1 | 7/2007 | Yu | |
| 2007/0213653 A1 | 9/2007 | Childers et al. | |
| 2008/0242915 A1 | 10/2008 | Jackson et al. | |
| 2008/0300570 A1 | 12/2008 | Fowles et al. | |
| 2008/0311007 A1 | 12/2008 | Helmerson | |
| 2009/0036864 A1 | 2/2009 | Moy et al. | |
| 2009/0057258 A1 | 3/2009 | Tornqvist | |
| 2009/0069783 A1 | 3/2009 | Ellstrom et al. | |
| 2009/0204066 A1 | 8/2009 | Radmer et al. | |
| 2009/0295385 A1* | 12/2009 | Brazdeikis | A61B 5/04005 324/309 |
| 2010/0004602 A1 | 1/2010 | Nord et al. | |
| 2010/0030048 A1 | 2/2010 | Heller et al. | |
| 2010/0042048 A1 | 2/2010 | Christensen | |
| 2010/0084041 A1 | 4/2010 | Fehr et al. | |
| 2010/0113891 A1 | 5/2010 | Barrett et al. | |
| 2010/0179506 A1 | 7/2010 | Shemesh et al. | |
| 2011/0004143 A1 | 1/2011 | Beiriger et al. | |
| 2011/0004144 A1 | 1/2011 | Beiriger et al. | |
| 2011/0004145 A1 | 1/2011 | Beiriger et al. | |
| 2011/0004187 A1 | 1/2011 | Beiriger | |
| 2011/0009800 A1 | 1/2011 | Dam et al. | |
| 2011/0054397 A1 | 3/2011 | Menot et al. | |
| 2011/0077614 A1 | 3/2011 | Shay | |
| 2011/0094619 A1 | 4/2011 | Steel et al. | |
| 2011/0118662 A1 | 5/2011 | Mhatre et al. | |
| 2011/0125085 A1 | 5/2011 | McGill et al. | |
| 2011/0152770 A1 | 6/2011 | DiPerna et al. | |
| 2011/0160701 A1 | 6/2011 | Wyatt et al. | |
| 2011/0172603 A1 | 7/2011 | Yodfat et al. | |
| 2011/0190702 A1 | 8/2011 | Stumber | |
| 2011/0190703 A1 | 8/2011 | Pratt et al. | |
| 2011/0232388 A1* | 9/2011 | Butterfield | A61B 5/021 73/705 |
| 2012/0203476 A1 | 8/2012 | Dam | |
| 2012/0209171 A1 | 8/2012 | Vedrine et al. | |
| 2012/0258545 A1 | 10/2012 | Ash et al. | |
| 2013/0018354 A1 | 1/2013 | Sund et al. | |

FOREIGN PATENT DOCUMENTS

| | | |
|---|---|---|
| EP | 0532432 | 9/1991 |
| EP | 1978256 | 10/2008 |
| GB | 2098670 | 11/1982 |
| WO | WO1996040322 A1 | 12/1996 |
| WO | WO1999010027 A1 | 3/1999 |
| WO | WO2006011009 A3 | 4/2006 |
| WO | WO2007101798 A2 | 9/2007 |
| WO | WO2008008845 A2 | 1/2008 |
| WO | WO2008009288 A1 | 1/2008 |
| WO | WO2008064046 A2 | 5/2008 |
| WO | WO2009044221 A1 | 4/2009 |
| WO | WO2009097159 A8 | 11/2009 |
| WO | WO2010099816 A1 | 9/2010 |
| WO | WO2010100074 A3 | 12/2010 |
| WO | WO2011054693 A1 | 5/2011 |
| WO | WO2011092068 A1 | 8/2011 |

* cited by examiner

MAGNETIC SENSORS AND RELATED SYSTEMS AND METHODS

TECHNICAL FIELD

This invention relates generally to magnetic sensors and related systems and methods.

BACKGROUND

As soon as kidney failure is diagnosed, patients are typically given medication to help control the symptoms and slow the progress of the damage to the kidneys. Patients with chronic kidney failure generally take drugs to control the balance of minerals in the body and prevent a reduction of red blood cells (anemia).

Healthy kidneys produce the hormone erythropoietin (often shortened to "EPO"), which stimulates the production of red blood cells in the bone marrow. Red blood cells play a key role in the delivery of oxygen to tissues in the body. If the body does not have enough EPO, it can lead to anemia. This often causes a drop in physical and mental performance and an increased risk for cardio-vascular diseases. To prevent anemia, chronic renal patients normally receive a synthetic version of erythropoietin (also referred to as "EPO") that, like the natural erythropoietin, stimulates the production of red blood cells.

Anemia can be managed using a variety of different drugs. For example, since iron is also needed to produce red blood cells, many dialysis patients also take iron preparations. Venofer® (iron sucrose injection, USP) is indicated in the treatment of iron deficiency anemia in patients undergoing chronic hemodialysis who are receiving supplemental EPO therapy.

SUMMARY

In one aspect of the invention, a dialysis system includes a dialysis machine, a medical fluid tube connected to the dialysis machine, and a sensor assembly connected to the medical fluid tube. The sensor assembly includes a housing configured to releasably hold the medical fluid tube and a sensor secured to the housing. The sensor is configured to detect a change in strength of a magnetic field when a medical fluid passes through the medical fluid tube.

In another aspect of the invention, a magnetic sensor assembly includes a housing configured to releasably hold a medical fluid tube and a sensor secured to the housing, the sensor configured to detect a change in a strength of a magnetic field when a medical fluid passes through the medical fluid tube.

In another aspect of the invention, a medical fluid delivery method includes detecting a magnetic field of fluid in a medical fluid tube. The method also includes determining whether a drug is in the medical fluid tube based on the detection of the magnetic fluid.

In another aspect of the invention, a dialysis system includes a dialysis machine, a medical fluid tube connected to the dialysis machine, and a sensor assembly connected to the medical fluid tube. The sensor assembly includes a housing configured to releasably hold the medical fluid tube, a plurality of capacitor plates configured such that the medical tube is releasably held between the capacitor plates, and a circuit connected to the capacitor plates.

In another aspect of the invention, a capacitance sensor assembly includes a housing configured to releasably hold a medical fluid tube and a plurality of capacitor plates secured to the housing. The capacitor plates are configured to detect a change in a strength of a dielectric constant when a medical fluid passes through the medical fluid tube.

In another aspect of the invention, a medical fluid delivery method includes determining a capacitance between plates, the plates having a medical fluid tube between the plates and based on the detected capacitance, detecting whether the medical fluid tube contains a medical fluid.

Implementations can include one or more of the following features.

In certain implementations, the medical fluid includes a ferromagnetic fluid.

In certain implementations, the medical fluid tube includes a blood line.

In some implementations, a drip chamber is connected to the blood line, and the sensor assembly is connected to the blood line downstream of the drip chamber.

In certain implementations, the medical fluid line includes a drug delivery line.

In certain implementations, a drug delivery device is connected to the dialysis machine via the drug delivery line.

In certain implementations, a magnet is adjacent the medical fluid tube and located upstream of the sensor assembly and configured to magnetize the medical fluid that passes through the medical fluid tube.

In some implementations, the magnet is located at a distance of 0.1 inches or less from the sensor assembly.

In certain implementations, the dialysis system includes a data processing apparatus and a computer storage medium encoded with a computer program. The program includes instructions that when executed by the data processing apparatus cause the data processing apparatus to perform operations including receiving information regarding the detection of a change in strength of the magnetic field when the medical fluid passes through the medical fluid tube and determining whether the medical fluid is present in the medical fluid tube.

In some implementations, the operations include receiving information regarding desired flow rates of a first and second fluid through the medical fluid tube and determining whether actual flow rates of the first and second fluids are equal to the desired flow rates based on the flow rates and the detection of the change in magnetic field.

In certain implementations, the sensor is a magnetometer.

In certain implementations, the assembly includes a plurality of sensors configured to detect a change in the strength of the magnetic field when the medical fluid passes through the medical fluid tube.

In some implementations, the assembly includes a magnet secured to the housing, and the magnet is configured to magnetize the medical fluid when the medical fluid passes through the medical fluid tube.

In certain implementations, the assembly includes a data processing apparatus and a computer storage medium encoded with a computer program. The program includes instructions that when executed by the data processing apparatus cause the data processing apparatus to perform operations including receiving output data of the sensor and calculating whether the ferromagnetic fluid is present in the medical fluid tube based on the output data. The output data is related to the detected change in the strength of the magnetic field when the medical fluid passes through the medical fluid tube.

In certain implementations, the operations include calculating the amount of ferromagnetic fluid in the medical fluid tube based on the output data, the output data related to the detected change in the strength of the magnetic field when the medical fluid passes through the medical fluid tube.

In certain implementations, the operations include receiving information regarding the total amount of fluid in the medical fluid tube.

In some implementations, the operations include calculating the ratio of ferromagnetic fluid to non-ferromagnetic fluid in the medical fluid tube.

In certain implementations, the method is a computer-implemented method performed by a data processing apparatus.

In certain implementations, an output of the circuit indicates a change in capacitance when a medical fluid passes through the medical tube.

In some implementations, the change in capacitance comprises a change in a dielectric when the medical fluid passes through the medical tube.

In certain implementations, the operations include receiving information regarding the detection of a change in capacitance when the medical fluid passes through the medical fluid tube and determining whether the medical fluid is present in the medical fluid tube.

In certain implementations, the operations include receiving output data of the sensor and calculating whether the medical fluid is present in the medical fluid tube based on the output data. The output data is related to the detected change in the capacitance when the medical fluid passes through the medical fluid tube.

In certain implementations, the operations include calculating the amount of medical fluid in the medical fluid tube based on the output data, the output data related to the detected change in capacitance when the medical fluid passes through the medical fluid tube.

Implementations can include one or more of the following advantages.

In some implementations, the magnetic sensor detects whether a drug is being delivered to a patient by a drug delivery system. Detecting the presence of the drug can serve as an indication that the drug delivery system is functioning properly. For example, detecting the presence of the drug can serve as an indication that there are no leakages or stoppages in the medical fluid tubes and that the pumps are working properly.

In certain implementations, the magnetic sensor detects the amount (e.g., volumetric flow rate) of drug being delivered to the patient. The detected amount of drug can be used to verify the dosage of drug prescribed by the doctor and input to the system is actually being delivered to the patient.

In certain implementations, the magnetic sensor assembly can be used with opaque medical fluid tubes or medical fluid tubes with thick walls. As the magnetic sensor assembly uses changes in magnetic field to detect the drug, it is not significantly affected by optical factors such as the color of the medical fluid tube or the thickness of the walls.

In certain implementations, the magnetic sensor assembly can be used with medical fluid tubing with narrow fluid channels. As the magnetic sensor assembly uses changes in magnetic field to detect the drug, the sensor assembly does not need to align precisely with the fluid channel to detect the drug.

DETAILED DESCRIPTION

In general, the invention relates to magnetic sensors and systems and methods that use magnetic sensors. In some aspects of the invention, a hemodialysis system includes a hemodialysis machine having a blood circuit connected to a drug delivery device via a drug delivery line such that drug can be delivered to the blood circuit via the drug delivery line. A magnetic sensor is configured to detect the drug passing through the drug delivery line and/or a blood line of the blood circuit. Thus, the magnetic sensor can be used to confirm that the drug is being delivered to the patient. In some cases, the magnetic sensor can be used to confirm that the desired amount of the drug is being delivered to the patient.

Figure 1:
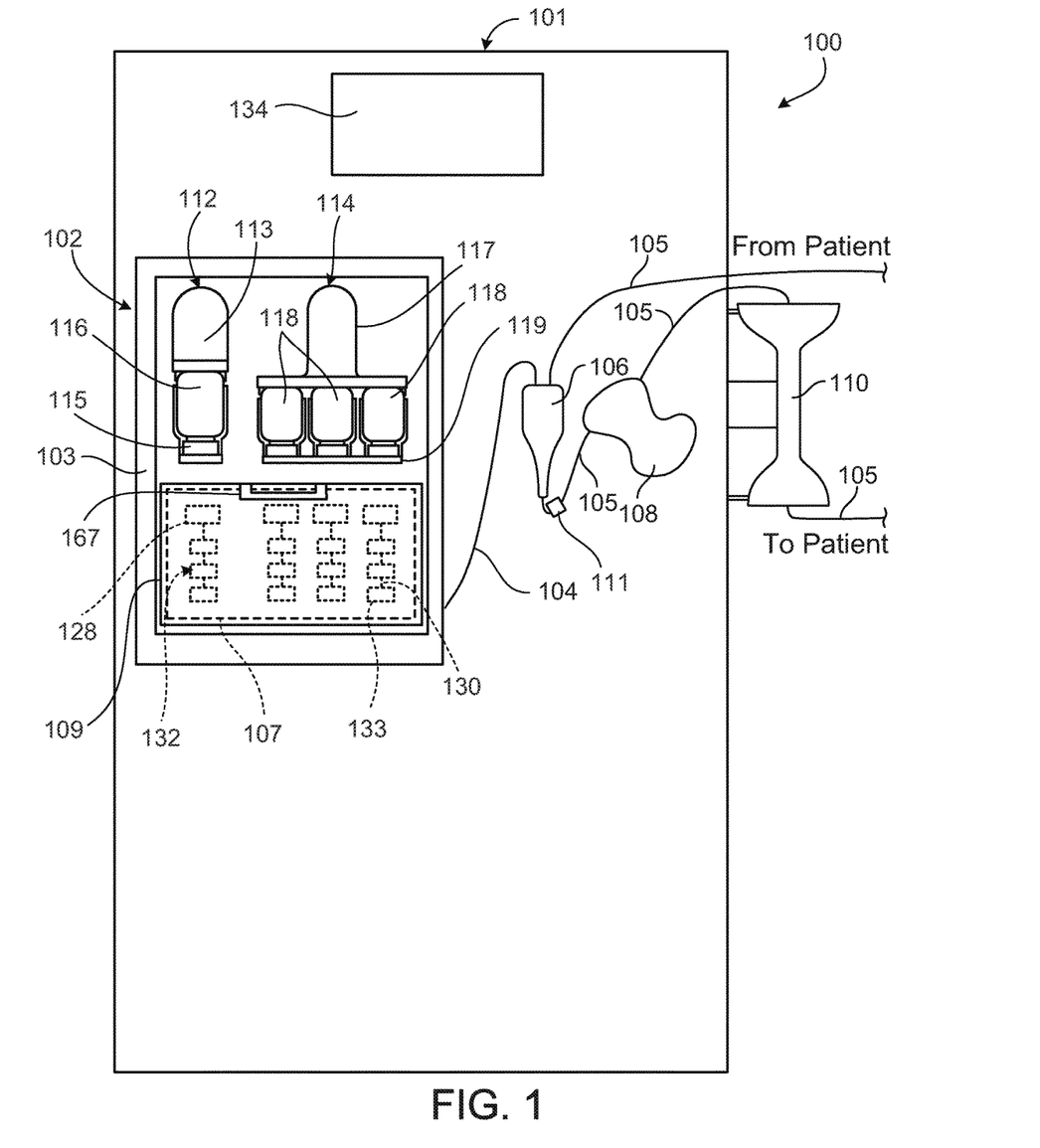
FIG. 1 is a schematic of a hemodialysis machine that includes a modular drug delivery device and a drug administration fluid line cassette secured between a door and inner face of the modular drug delivery device. The hemodialysis machine further includes a magnetic sensor assembly that can be used to determine whether certain types of drugs have been introduced into a blood line engaged with the magnetic sensor assembly.

Referring to FIG. 1, a hemodialysis system 100 includes a hemodialysis machine 101 equipped with a drug delivery system 102. The drug delivery system 102 includes a modular drug delivery device 103 that is attached to and exposed on the face of the hemodialysis machine 101 and a disposable drug administration fluid line set (also referred to herein as a drug administration fluid line cassette) 107 that is connected to the drug delivery device 103. A drug delivery line 104 of the drug administration fluid line cassette 107 is fluidly connected to a blood circuit of the hemodialysis system 100. The blood circuit of the hemodialysis system 100 includes, among other things, a series of blood lines 105, a drip chamber 106, and a dialyzer 110. A blood pump (e.g., a peristaltic pump) 108 is configured to pump blood through the blood circuit during treatment.

The hemodialysis system 100 also includes a dialysate circuit and various other components that, for the sake of simplicity, are not described in detail. During hemodialysis treatment, blood is drawn from the patient and, after passing through the drip chamber 106, is pumped through the dialyzer 110 where toxins are removed from the blood and collected in dialysate passing through the dialyzer. The cleansed blood is then returned to the patient, and the dialysate including the toxins (referred to as "spent dialysate") is disposed of or recycled and reused. As discussed in greater detail below, during the hemodialysis treatment, drugs (e.g., Epogen® and Venofer®) are also delivered to the drip chamber 106 using the drug delivery system 102. The drugs mix with the patient's blood within the drip chamber 106 and are then delivered to the patient along with the patient's blood.

A magnetic sensor assembly 111 extends from the face of the hemodialysis machine 101, and the blood line 105 that connects the drip chamber 106 to the blood pump 108 is releasably secured to (e.g., snapped into) the magnetic sensor assembly 111. As will be described in greater detail below, the magnetic sensor assembly 111 can be used to detect the presence of a drug delivered into the blood circuit by the drug delivery system 102 and, in certain cases, can be used to confirm that a desired amount of the drug has been delivered into the blood circuit.

Figure 3:
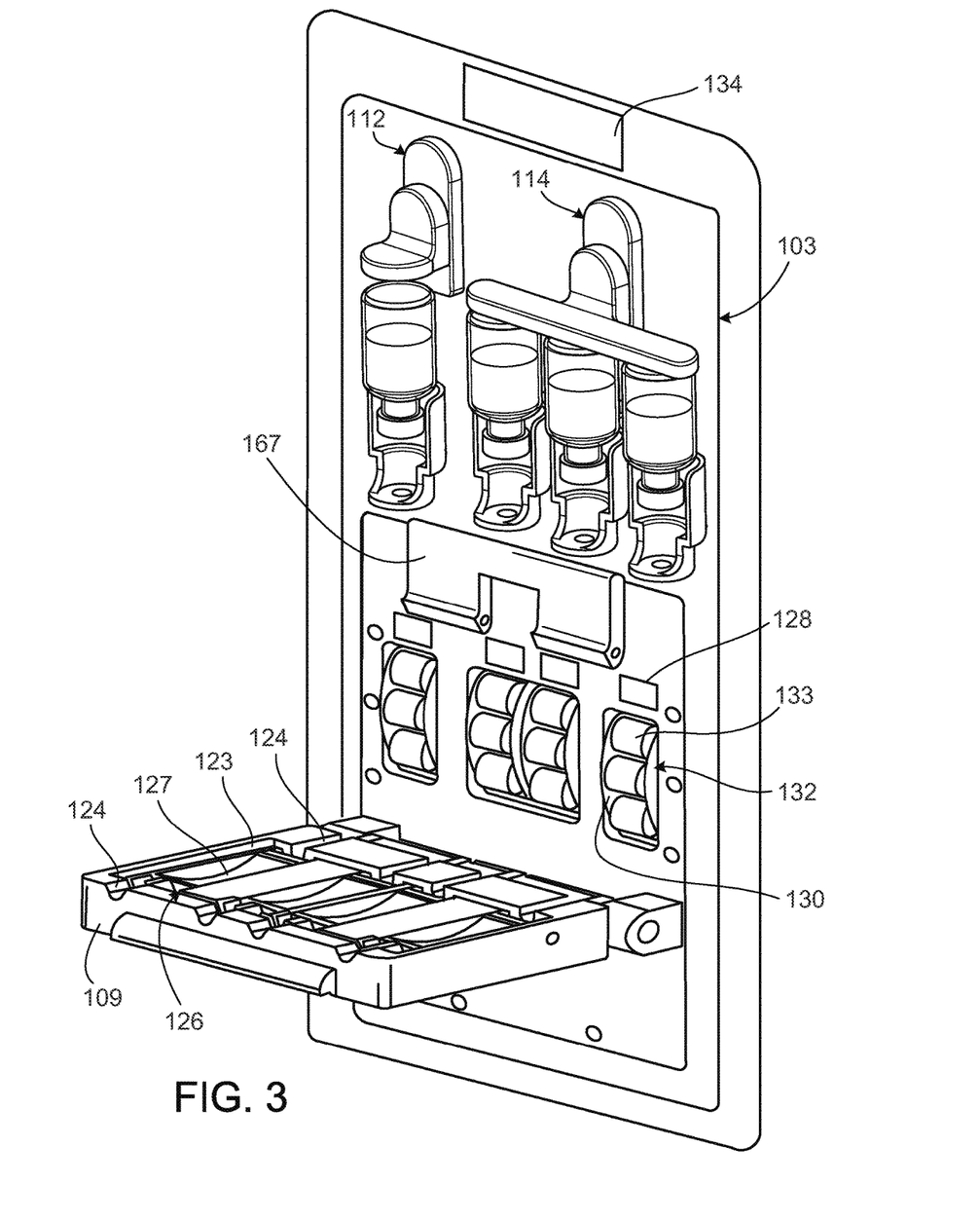
FIG. 3 is a perspective view of the hemodialysis machine of FIG. 1 with the door of the drug delivery device opened.

As shown in FIG. 3, the modular drug delivery device 103 includes a drug vial holder 112 configured to hold a single drug vial 116. Another drug vial holder 114 is configured to hold up to three drug vials 118. In the illustrated implementation, the vial 116 furthest to the left contains Venofer® and the three vials 118 to the right of the Venofer® vial 116 contain Epogen®.

Epogen® is a drug (i.e., synthetic erythropoietin) that stimulates the production of red blood cells and is also commonly used in dialysis patients. Epogen® is manufactured by Amgen, Inc.

Venofer® (iron sucrose injection, USP) is a sterile, aqueous complex of polynuclear iron (III)-hydroxide in sucrose that is manufactured by American Regent, Inc. Venofer® is indicated in the treatment of iron deficiency anemia in patients undergoing chronic hemodialysis who are receiving supplemental erythropoietin therapy. Venofer® is a ferromagnetic fluid, i.e., a fluid that is affected by magnets and magnetic fields. Thus, the ferromagnetic properties of the Venofer® allow the magnetic sensor assembly 111 to determine, based on changes in a magnetic field, whether Venofer® is flowing through the tube engaged with the magnetic sensor assembly 111 and, in some cases, allow the magnetic sensor assembly 111 to detect the amount (e.g., volumetric flow rate) of Venofer® that is flowing through the tube. This process will be explained in greater detail below.

The drug vial holder 112 includes a top member 113 and a bottom member 115 that can retain the single Venofer® vial 116 therebetween. The bottom member 115 has a top surface on which the cap of the inverted Venofer® vial 116 can rest. In certain implementations, the bottom member 115 includes a recess that is sized and shaped to receive a cap (or a portion of the cap) of the vial 116. This recess can help to ensure that the vial 116 is properly positioned in the vial holder 112. The bottom member 115 of the drug vial holder 112 also defines a through opening that allows an associated spike 120 of the drug administration fluid line cassette 107 to pass through the bottom member 113 and pierce a rubber seal of the Venofer® vial 116 during use.

The top and bottom members 113, 115 of the drug vial holder 112 are moveable relative to one another such that a drug vial can be compressed therebetween. In addition, the drug vial holder 112 as a whole is moveable in the vertical direction relative to the inner face of the drug delivery device 103 and relative to an associated spike 120 of the drug administration fluid line cassette 107 when the drug administration fluid line cassette 107 is disposed in the cassette compartment of the drug delivery device 103. As a result, when the cassette 107 is disposed in the cassette compartment, the top and bottom members 113, 115 of the drug vial holder 112 can be moved in unison along with the Venofer® vial 116 to cause the associated spike 120 of the cassette 107 to pierce the rubber seal of the vial 116.

The drug vial holder 114, which holds the Epogen® vials 118 during use, is similar to the drug vial holder 112 described above. In particular, this drug vial holder 114 also includes top and bottom members 117, 119 between which three Epogen® vials 118 can be held, and the bottom member 119 defines three openings through which spikes 120 of the cassette 107 can pass to pierce rubber seals of the vials 118. In some implementations, the upper surface of the bottom member 119 defines recesses that receive the caps of the Epogen® vials 118 and help to ensure that the vials 118 are properly positioned in the vial holder 114. These recesses can, for example, help to ensure that the vials 118 are aligned with the openings in the bottom member 119 to allow the spikes 120 of the cassette 107 to pierce the rubber seals of the vials 118.

Figure 2:
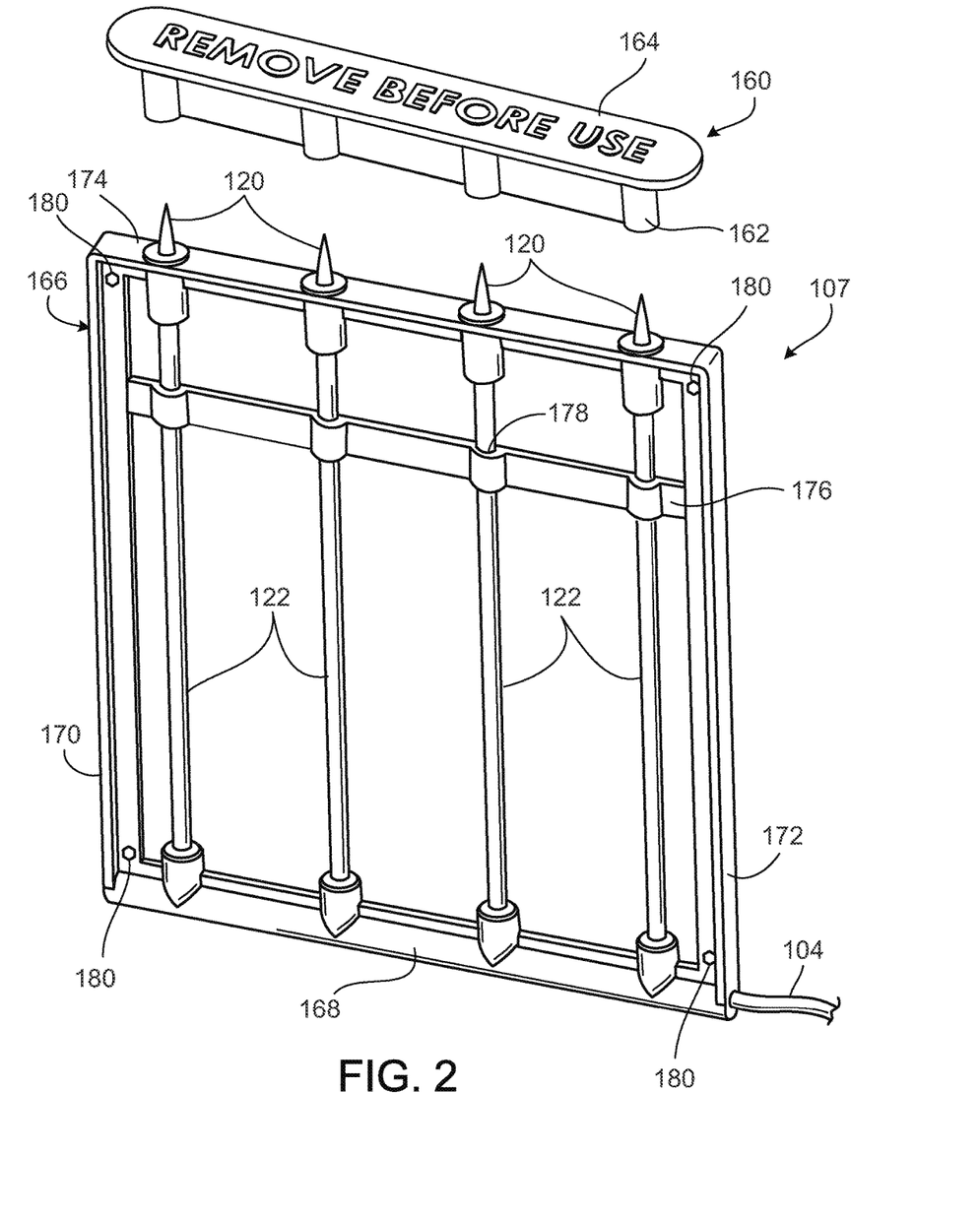
FIG. 2 is a perspective, exploded view of the drug administration fluid line cassette that is partially illustrated in FIG. 1 and a spike cover that is disposed over spikes of the drug administration fluid line cassette prior to use.

FIG. 2 illustrates the drug administration fluid line cassette 107 with a protective spike cover 160 removed from the spikes 120. As shown, feeder lines 122 are retained in a spaced apart configuration by a frame 166 of the cassette 107. The frame 166 includes along its bottom edge a manifold 168 that connect the feeder lines 122 to the drug delivery line 104, two side support members 170, 172 that extend from the manifold 168, and a top support member 174 that extends between the two side support members 170, 172. The side support members 170, 172 are attached (e.g., thermally bonded, adhesively bonded, or mechanically attached) at their bottom and top ends to the manifold 168 and top support member 174, respectively. The feeder lines 122 similarly extend between and are attached (e.g., thermally bonded, adhesively bonded, or mechanically attached) to the manifold 168 and top support member 174.

In addition to the frame 166, the cassette 107 includes a crossbar 176 that extends between the two side support members 170, 172. The crossbar 176 includes recessed regions 178 into which the feeder lines 122 are received and retained. In addition, hexagonal holes 180 are provided in the front surface of the cassette 107 (i.e., the surface of the cassette 107 that contacts the inner surface of a door 109 of the drug delivery device 103 when the cassette 107 is loaded in the cassette compartment of the drug delivery device 103). As described below, these holes 180 mate with hexagonal projections extending from the inner surface of the door 109 to secure the cassette 107 to the door 109 during use and to help ensure that only appropriate cassettes (e.g., cassettes intended for use with the drug delivery device 103 by the drug delivery device manufacturer) are used with the drug delivery device 103.

Still referring to FIG. 2, the spikes 120 are attached (e.g., thermally bonded, adhesively bonded, and/or mechanically attached) to and extend upward from the top support member 174 of the cassette 107. The drug vial spikes 120 can be formed of one or more relatively rigid medical grade plastics, such as polycarbonate or alphamethylstyrene (AMS), and the various fluid lines can be formed of a more flexible medical grade plastic, such as polyvinylchloride (PVC). Each of the spikes 120 can include, for example, a central channel that extends along the length of the spike and two openings (e.g., channels or slots) along the outer surface of the spike that lead to the central channel. The central channel of each spike is aligned with and fluidly connected to a vertical passage extending through the top support member 174.

The feeder lines 122 are in fluid communication with their associated spikes 120 via the vertical passages extending through the top support member 174. The feeder lines are also in fluid communication (via openings in the top surface of the manifold 168) with the central passage that extends through the manifold 168. The drug delivery line 104 is similarly connected to the manifold 168 and is in fluid communication with the central passage of the manifold

168. Thus, when the spikes 120 penetrate the rubber seals of the vials 116, 118 during use, drug can flow through the feeder lines 122, the manifold 168, the drug delivery line 104, and into the drip chamber 106.

The manifold 168, the side support members 170, 172, the top support member 174, and the crossbar 176 are typically formed of one or more materials that are more rigid than the material or materials from which the feeder lines 122 are made. Examples of such relatively rigid materials include polycarbonate and AMS. However, other relatively rigid materials can alternatively or additionally be used. Due to the construction and materials of the frame 166 and cross bar 176 of the cassette 107, the feeder lines 122 are held in substantially fixed positions relative to one another. As a result of this configuration, loading of the drug administration fluid line cassette 107 into the cassette compartment of the drug delivery device 103 is simplified.

Still referring to FIG. 2, the spike cover 160 is a unitary plastic structure that includes multiple tubular members 162 extending downward from an elongate structure 164. The tubular members 162 form cavities in which the drug vial spikes 120 of the cassette 107 are disposed prior to their insertion into the vials 116, 118. The cavities are sized and shaped so that the portions of the tubular members 162 forming those cavities grip their associated spikes 120 with sufficient force to prevent the cover 160 from falling off or being inadvertently knocked off the spikes 120 prior to loading the vials 116, 118 onto the spikes 120, while allowing the operator of the system to manually remove the cover 160 from the spikes 120 at the desired time. The spike cover 160 is removed form the spikes 120 of the cassette 107 prior to loading the vials 116, 118 onto the spikes 120.

Referring again to FIG. 1, which illustrates the cassette 107 in the cassette compartment of the drug delivery device 103, the spikes 120 of the cassette 107 have been inserted into the vials 116 and 118, which are retained in vial holders 112 and 114, respectively. Peristaltic pumps 132 extend from the inner face of the drug delivery device 103 and align with the feeder lines 122 (between the cross bar 176 and the manifold 168 of the cassette 107) such that when one of the pumps 132 is operated, the drug is drawn from the vial 116, 118 associated with that pump and delivered via the feeder lines 122, the manifold 168, and the drug delivery line 104 to the drip chamber 106 of the blood circuit.

Each of the feeder lines 122, as shown also in FIG. 3, passes through (e.g., is threaded through) a bubble detector 128, arranged in a spaced configuration across the inner face of the drug delivery device 103 above the peristaltic pumps 132. The bubble detectors 128 are capable of detecting air bubbles within the feeder lines 122. As a result, each of the bubble detectors 128 can determine whether its associated drug vial 116, 118 is empty during treatment, because air is drawn from the vial 116, 118 into the feeder line 122 when the vial is empty. In some implementations, the bubble detectors 122 are optical detectors. The OPB 350 bubble detector made by Optek can, for example, be used. Other types of optical detectors can alternatively or additionally be used. Similarly, other types of sensors, such as sensors utilizing ultrasound technology can be used as the bubble detectors. Examples of such sensors include the AD8/AD9 Integral Ultrasonic Air-In-Line, Air Bubble Detector and the BD8/BD9 Integral Ultrasonic Air Bubble, Air-In-Line & Liquid Level Detection Sensors (manufactured by Introtek International (Edgewood, N.Y.)). In some implementations, the bubble detector 128 includes a sensor that, in addition to sensing the presence of an air bubble within its associated feeder line 122, can sense the presence of the feeder line itself.

FIG. 3 illustrates the drug delivery device 103 with the door 109 opened and the drug administration fluid line cassette 107 removed. As shown, the inner surface of the door 109 includes a recessed region 123 that is configured to receive the rigid frame 166 of the cassette 107 and elongate slots 124 that are configured to receive the feeder lines 122 of the cassette 107 without substantially deforming the feeder lines 122. In certain implementations, the recessed region 123 and slots 124 are sized so that the frame 166 and feeder lines 122 of the cassette 107 can be snapped into the recessed region 123 and slots 124, respectively, and thus releasably secured to the door 109. The inner surface of the door 109 also includes the hexagonal projections that are configured fit into the hexagonal holes 180 formed in the cassette 107 when the cassette 107 is loaded into the door 109. The hexagonal projections can be sized and shaped to create a snap fit or a snug press fit that secures the drug administration fluid line cassette 107 to the door 109.

In addition, the inner surface of the door 109 includes spring-loaded members 126 that define recesses or raceways 127 that receive roller members of the peristaltic pumps 132 of the drug delivery device 103 when the door 109 is closed. Springs are connected to top and bottom regions of each member 126 and to an internal fixed member in the door 109 to allow the members 126 to flex in response to contact with the rollers of the peristaltic pumps 132 or in response to contact with the feeder lines 122 positioned between the members 126 and the rollers of the peristaltic pumps 132.

Still referring to FIG. 3, the peristaltic pumps 132 are positioned in a spaced configuration across the face of the drug delivery device 103. Each pump 132 includes multiple rollers 133 that compress the associated feeder line 122 in a manner to create a "pillow" of fluid (i.e., a "pillow" of air or liquid) that is pinched between two points of the feeder line 122 that are compressed by the pump rollers 133. The rollers 133 are arranged around a circumference of a rotatable frame. As the frame is rotated, the rollers 133 force the "pillow" of fluid through the feeder line 122 to the drug delivery line 104. The peristaltic pumps 132 are configured to rotate about an axis that extends in a direction that is substantially parallel to the face of the drug delivery device 103. When the cassette 107 is positioned in the cassette compartment between the inner face of the drug delivery device 103 and the closed door 109, the feeder lines 122 align with the pumps 132 and are thus pressed into the raceways 127 of the spring-loaded members 126 in the door 109. The spring force provided by the springs of the spring-loaded members 126 helps to take up tolerance between the raceways 127 and the rollers 133, and thus helps to ensure that a fixed compression force is applied to the feeder lines positioned between the raceways 127 and the rollers 133.

During operation of the pump 132, the rollers 133 are rotated from top to bottom (in the view shown in FIG. 3) and thus force pillows of fluid downward through the associated feeder line 122. When the pump 132 is being operated, vacuum pressure is applied to the drug vial 116, 118 that is connected to the feeder line 122. In certain cases, the initial pressure in the drug vial 116, 118 is equal to the ambient pressure, and when all of the drug has been delivered, the ending pressure within the vial is about −10 psi. In other words, the pressure within the drug vial 116, 118 progresses from ambient to −10 psi as the drug is delivered. The pump 132 is configured to generate a vacuum pressure within the feeder line 122 that exceeds the competing vacuum within the drug vial 116, 118. As a result, the drug is drawn from the vial 116, 118, through the drug vial spike 120 and into the feeder line 122.

The spacing of the rollers 133 about the circumference of the rotatable frames 130 of the peristaltic pumps 132 is selected so that at least one of the rollers 133 is positioned in the raceway 127 of the associated spring-loaded member 126 when the door 109 of the drug delivery device 103 is closed. This helps to ensure that the feeder lines 122 positioned between the pumps 132 and the raceways 127 are always occluded in at least one location and thus helps to prevent the drugs from passing through the feeder lines 122 to the manifold 168 when the pumps 132 are not in operation.

Referring again to FIGS. 1-3, the drug vial holders 112, 114 of the drug delivery device 103 can be equipped with various types of sensors for sensing the presence of a vial, identifying the type drug vial installed, detecting the size of the drug vials, and/or detecting the mass of the drug vials. In some implementations, each drug vial holder 112, 114 includes a sensor to sense the presence of a vial or drug container. In certain implementations, each drug vial holder 112, 114 includes a system which identifies the drug vial installed. The drug vial identification system can, for example, include a bar code reader that reads bar codes on the vials. Different types of sensors can alternatively or additionally be used. In some implementations, for example, the vial identification system uses RFID technology. Other examples of suitable sensors include color sensors for sensing the color of color-coded drug vials and/or for sensing the color of the drug within the vial, photo sensors (e.g., cameras) that are equipped with text recognition software to read text on the drug vial, capacitive sensors that permit different size vials to be detected, load cells or scales that detect the mass of the vial, and conductivity or electrical impedance sensors that can be used to determine the type of drug within the vial.

Figure 4A:
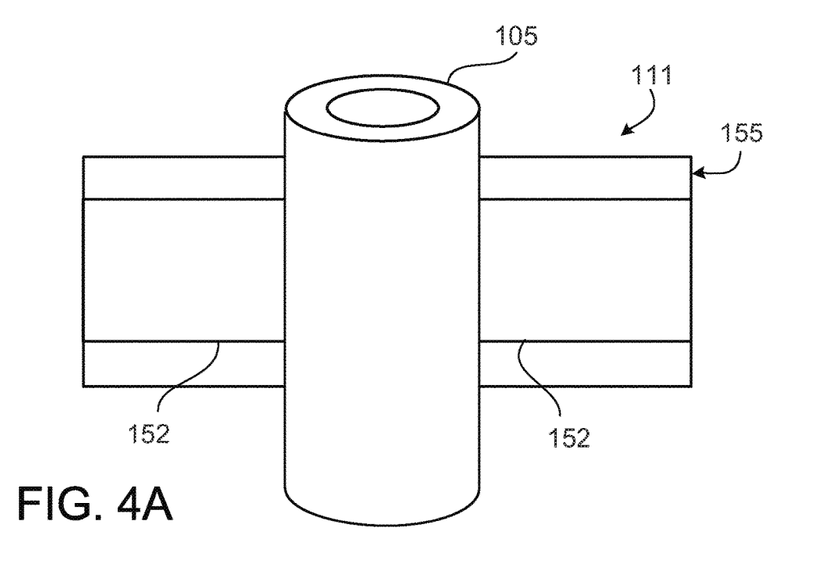
FIGS. 4A and 4B are top and cross-sectional schematic illustrations, respectively, of the magnetic sensor assembly of the hemodialysis machine of FIG. 1.
Figure 4B:
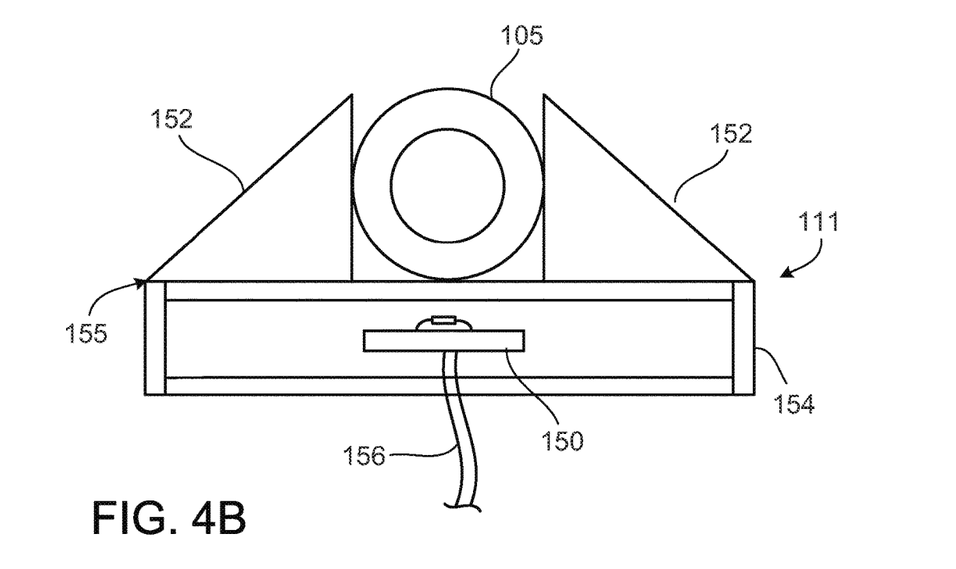

As described above, the hemodialysis machine 101 is equipped with the magnetic sensor assembly 111 for detecting Venofer® passing through the blood line 105 connected to the outlet part of the drip chamber 106. Referring to FIGS. 4A and 4B, the magnetic sensor assembly 111 includes a housing 155 configured to hold the blood line 105. The magnetic sensor assembly 111 is engaged with the blood line 105 downstream of the drip chamber 106. The housing 155 of the magnetic sensor assembly 111 includes two tubing guides 152 that protrude from a base 154. The tubing guides 152 are spaced apart on the base 154 of the housing 155 at a distance that is slightly less than the diameter of the blood line 105. This allows the blood line 105 to be friction fit between the tubing guides 152 so that the magnetic sensor assembly 111 securely retains the blood line 105 in a position aligned with a magnetic sensor 150 contained in the base 154 of the housing 155. The inner surfaces of the two tubing guides 152 that contact the blood line 105 are flat surfaces that protrude from the base 154 of the housing to a height that is slightly greater than the diameter of the blood line 105. From the inner surfaces to the edges of the housing 155, the tubing guides 152 taper down in height to the base 154 of the housing. The housing 155 can be formed of one or more relatively rigid medical grade plastics, such as polycarbonate or alphamethylstyrene (AMS), or any other relatively rigid, rugged, non-ferromagnetic material.

The magnetic sensor 150 is typically a Hall effect magnetometer. The magnetic sensor 150 outputs a voltage proportional to a magnetic field applied perpendicular to a surface of the sensor. As the magnetic field changes, the output voltage also changes. The presence of ferromagnetic fluids, such as Venofer®, in the blood line 105 affects the magnetic field sensed by the magnetic sensor 150. The magnetic sensor 150 transmits the signal corresponding to the sensed magnetic field to a control unit (e.g., a microprocessor) of the drug delivery device 103 through a wire 156 that is connected at one end to the magnetic sensor 150 and at its other end to the control unit. Thus, the magnetic sensor 150 can be used to detect the presence or absence of Venofer® in the blood line 105 and verify that the drug is being delivered as prescribed. If the presence of Venofer® detected by the magnetic sensor 150 when the control unit expects an absence, or vice versa, the control unit can cause an alarm and/or alert to be emitted.

In some implementations, the sensor 150 has a sensitivity of 2 mV/gauss to 10 mV/gauss. An example of a suitable sensor is an Analog Devices AD22151 Linear Output Magnetic Field Sensor.

The control unit of the drug delivery device 103 can also power the various components of the drug delivery device 103. The control unit can receive signals from and send signals to the various components of the drug delivery device 103 and hemodialysis machine 101, including, but not limited to, the magnetic sensor assembly 111, the bubble detectors 128, the peristaltic pumps 132, the drug vial ID sensors, and other sensors along the drug lines. For example, the control unit can be hard wired to these components. The control unit can control the various components of the drug delivery device 103 based on information received from these components.

The control unit can control the pumps 132 to ensure that only one of the pumps 132 is in operation at a time. This helps to ensure that drug is pulled from only one of the vials 116, 118 at a time during treatment. Upon determining that the prescribed volume of the drug has been delivered (based on monitoring the operation of the pumps 132), the control unit can turn off the pump 132 associated with that drug vial 116, 118 and turn on the pump 132 associated with the drug vial 116, 118 containing the next drug to be delivered. In addition, after the full contents of a vial have been evacuated, air will be sucked into the feeder line 122 associated with that vial and will be detected by the bubble detector 128. In response, the control unit can turn off the pump 132 associated with the empty vial and turn on the pump 132 associated with the vial containing the next drug to be delivered.

The control unit can also control certain components of the drug delivery device 103 based on signals received from the drug vial ID sensors, which indicate the presence of a vial and/or the identity of the vial contents. Such an arrangement can help to ensure that the correct vials (e.g., the correct number of vials and the vials containing the correct contents) are used for the treatment. Upon receiving signals from the drug vial ID sensors that do not match the inputted treatment information, for example, an alarm (e.g., an audible and/or visual alarm) can be activated. Alternatively or additionally, the drug delivery device 103 can be configured so that treatment cannot be initiated until the sensors detect the correct combination of vials.

The drug delivery device 103 (e.g., the control unit of the drug delivery device 103) is configured to sense if the blood pump 108 of the dialysis machine 101 is running and to pause drug delivery if the blood pump 108 is stopped. This technique prevents "pooling" of the delivered drug in the drip chamber 106 during treatment.

Still referring to FIGS. 1-3, the hemodialysis machine 101 includes a user interface 134 that is connected to the control unit. The user interface 134 includes keys that allow the user to navigate through displays associated with the vials 116, 118 and set the desired dosage for each of the vials 116, 118. In addition, the user interface 134 includes start and stop keys that allow the user to start and stop the drug delivery device 103.

Any of various other types of user interfaces can alternatively or additionally be used. In some implementations, the drug delivery device includes a user interface that allows the user to select a drug to infuse from a menu. In certain implementations, the user may confirm that the drug identified by the drug vial ID sensor is correct and/or make appropriate adjustments. The user interface can be used to input and/or monitor various different treatment parameters. Examples of such parameters include drug dosage, drug delivery rate, amount of drug delivered, status of the drug delivery for each drug channel, time, percent complete, percent remaining, time remaining, time delivered, date, patient ID, patient name, alarms, alerts, etc. Such user interfaces can include a color graphical display. In certain implementations, for example, the user interface is color coded according to drug, dosing, or status of drug delivery (e.g., done, running, ready, etc.).

The hemodialysis machine 101 also includes an alarm and/or alert system to which the control unit of the hemodialysis machine 101 is connected. The alarm and/or alert system can be configured to emit a visual and/or audio alarm and/or alert. The alarm and/or alert system can further include pre-programmed alarm and/or alert limitations so that when a user modifies any aspect of the system to be outside of the limitations, or the machine itself detects any aspects of the system to be outside of the limitations, the alarm and/or alert system emits an alarm and/or alert. In some implementations, this system utilizes the user interface 134 to emit a visible alert and/or speakers of the hemodialysis machine 101 to emit an audible alert. Alternatively, this system can be an independent system that is separate from the user interface 134.

Still referring to FIGS. 1-3, a method of using the hemodialysis system 100 to perform hemodialysis on a patient will now be described. Prior to beginning hemodialysis treatment on a patient, the various lines that make up the blood circuit and dialysate circuit of the hemodialysis machine are primed, and then the patient lines 105 are connected to the patient. After connecting the patient lines 105 to the patient, the blood pump 108 is activated to circulate blood through the blood circuit. A dialysate pump is also activated to pump dialysate through the dialysate circuit of the hemodialysis machine. The blood is drawn from the patient and delivered to the drip chamber 106 via the arterial patient line. The drip chamber 106 acts as an air trap such that any air in the blood is released as the blood passes through the drip chamber 106. In particular, the drip chamber 106 includes a vent through which air released from the blood can be vented from the drip chamber 106. The blood is then pumped from the drip chamber 106 to the dialyzer 110, which includes a semi-permeable membrane that divides the dialyzer 110 into two chambers. As the blood passes through one of the chambers of the dialyzer 110, dialysate from the dialysate circuit passes through the other chamber. As the blood flows by the dialysis fluid, impurities, such as urea and creatinine, diffuse through the semi-permeable membrane into the dialysate. The spent dialysate is either disposed of or recycled and reused. The cleansed blood exiting the dialyzer 110 is returned to the patient via the venous patient line.

After initiating the hemodialysis treatment, the operator of the hemodialysis system 100 (e.g., the physician, nurse, medical assistant, or patient) determines the prescribed Epogen® dose and then consults a dosing schedule for the different vial combinations that can be used to deliver the prescribed Epogen® dose. Examples of suitable dosing schedules are described in U.S. patent application Ser. No. 12/827,119, which is herein incorporated by reference in its entirety. The operator then selects one of the Epogen® vial combinations provided based on the operator's preference and loads the selected Epogen® vials into the drug vial holders. The operator also loads a vial of Venofer® into one of the drug vial holders.

The operator of the system then loads the drug administration fluid line cassette 107 into the door 109 of the drug delivery device 103. After loading the drug administration fluid line cassette 107 onto the door 109, the operator closes the door 109 and secures a latch 167 to hold the door 109 in the closed position. Because the cassette 107 is securely fastened to the door 109 in a desired position, the feeder lines 122 align with their associated pumps 132 and bubble detectors 128 when the door 109 is closed. Thus, as the door 109 is closed, the protruding peristaltic pumps 132 press the feeder lines 122 into the raceways 127 formed along the inner surface of the door 109, and the inner surface of the door 109 presses the feeder lines 122 into engagement with the bubble detectors 128. With the door 109 in the closed position, the spikes 120 of the cassette 107 rest directly below the holes formed in the bottom members 115, 119 of the vial holders 112, 114.

The prescribed dosages of Venofer® and Epogen® are then entered into the drug delivery device 103 using the user interface 134 of the hemodialysis machine 101 with which the control unit of the drug delivery device 103 is in communication. Alternatively or additionally, the prescribed dosage of Venofer® and Epogen® can be electronically transmitted to the control unit of the drug delivery device 103 from a database or website accessible by the patient's prescribing physician. The operator, after reviewing the prescribed dosage entered into or transmitted to the machine, confirms that the prescribed dosage is correct by pressing a button (e.g., an "Accept" or "Confirm" button) on the user interface 134 of the hemodialysis machine 101, which initiates the spiking and priming process.

After spiking the vials 116, 118, the feeder lines 122 of the drug administration fluid line cassette 107 are primed by activating the pumps 132, either sequentially or simultaneously, which causes a portion of the drug to be drawn from each of the vials 116, 118. During the priming process, each pump 132 remains on until the drug from its associated vial 116, 118 is detected by the bubble detector 128, at which point the pump 132 is stopped and pinches off or occludes that feeder line 122. If the drug is not detected by one of the bubble detectors 128, an alarm can be activated prompting the operator to replace or adjust the drug administration fluid line cassette 107 and repeat the priming process.

After priming the feeder lines 122, Venofer® is delivered from the Venofer® vial 116 to the drip chamber 106 by activating the pump 132 associated with the Venofer® vial 116 (while leaving all of the other pumps off). While delivering Venofer®, the magnetic sensor assembly 111 monitors fluid passing through the tube to confirm that Venofer® is being properly delivered. If there is no detection of Venofer®, an alarm is activated. In response, the user can check for kinks or blockages in the drug delivery line 104 and the Venofer® feeder line 122. Upon determining that the prescribed dosage of Venofer® has been delivered (e.g., by monitoring operation of the peristaltic pump 132 associated with the Venofer® vial) to the drip chamber 106, the control unit causes the pump 132 associated with the Venofer® feeder line to be turned off.

As the magnetic sensor assembly 111 is placed on the blood line 105 downstream of the drip chamber, the fluid that passes through the blood line 105 at the point of the magnetic sensor assembly 111 typically contains a mixture of Venofer® and blood. The Venofer® is detected by the magnetic sensor assembly 111 by the change in magnetic field. Any change in magnetic field caused by the blood, specifically the iron contained in the blood, can be factored into the detection system. For example, the default magnetic field reading can be one with blood already in the blood line 105. Alternatively or additionally, the change in the magnetic field caused by the presence of blood can be subtracted from the total change in the magnetic field.

The pump associated with the first Epogen® vial 118 (i.e., the Epogen® vial directly to the right of the Venofer® vial 116) is then activated such that Epogen® is delivered to the drip chamber 106. When the bubble detector 128 detects air in the feeder line 122, a signal is sent to the control unit, indicating that the first Epogen® vial 118 is empty. The control system then sends a signal causing the pump associated with the first Epogen® vial 118 to be turned off after assuring that an additional known volume is pumped so that the Epogen® in the line downstream of the bubble detector 128 is flushed down to a segment where the delivery of drug from the next vial can push that Epogen® remaining in the line to the drip chamber 106. In particular, the control unit ensures that the additional pumped volume is sufficient to push the Epogen® past the pump 132 and into the passage of the manifold 168 such that the next volume of drug delivered will push the Epogen® to the drip chamber 106. The control unit also sends a signal to activate the pump 132 associated with the second Epogen® vial 118 (i.e., the Epogen® vial directly to the right of the first Epogen® vial). The Epogen® delivery process described above is then repeated for the second and third Epogen® vials.

After delivering the desired amounts of Venofer® and Epogen® to the drip chamber 106, the drug delivery device 103 is deactivated and the drug administration fluid line cassette 107 and vials 116, 118 are removed from the drug delivery device 103 and discarded.

In some implementations, the Venofer® and Epogen® are simultaneously delivered to the drip chamber 106. In such implementations, the controller can be configured to determine a ratio of Venofer® to Epogen® passing through the blood line. For example, prior to programming the controller, a series of experiments can be run to determine the change produced on a magnetic field by different ratios of Venofer® to Epogen®. The corresponding voltages from the magnetic sensor and ratios of Venofer® to Epogen® can be stored in a lookup table that is accessible to the controller. The controller can use the look up table to determine the ratio of Venofer® to Epogen® upon receiving a voltage reading from the magnetic sensor.

While the magnetic sensor 150 has been shown to be located at the bottom of the housing of the magnetic sensor assembly 111, alternative configurations are possible. For example, the magnetic sensor can be located on either side of the housing, in the tubing guides.

Figure 5A:
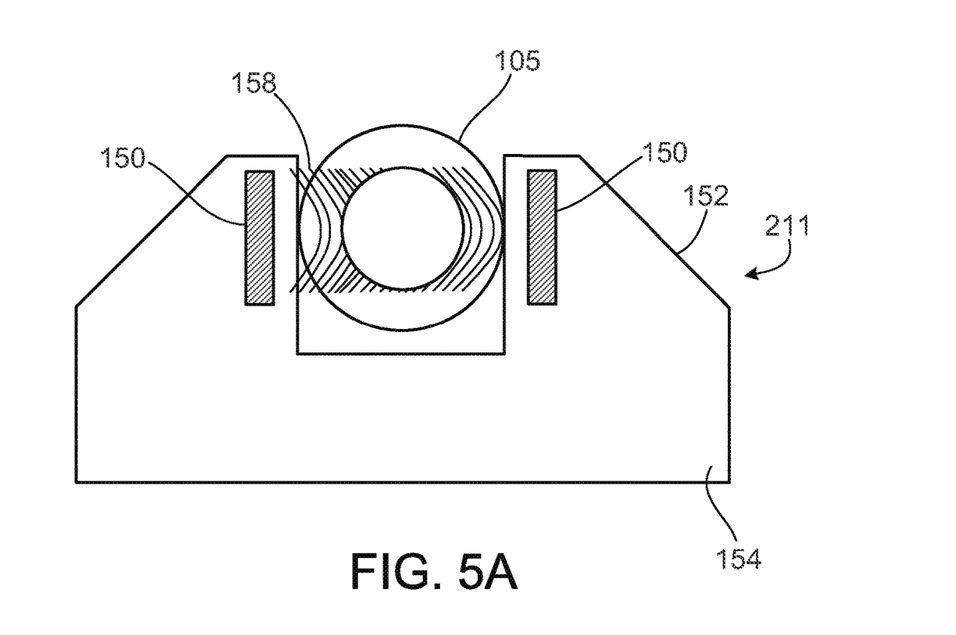
FIGS. 5A and 5B are schematic diagrams of another magnetic sensor assembly during use.
Figure 5B:
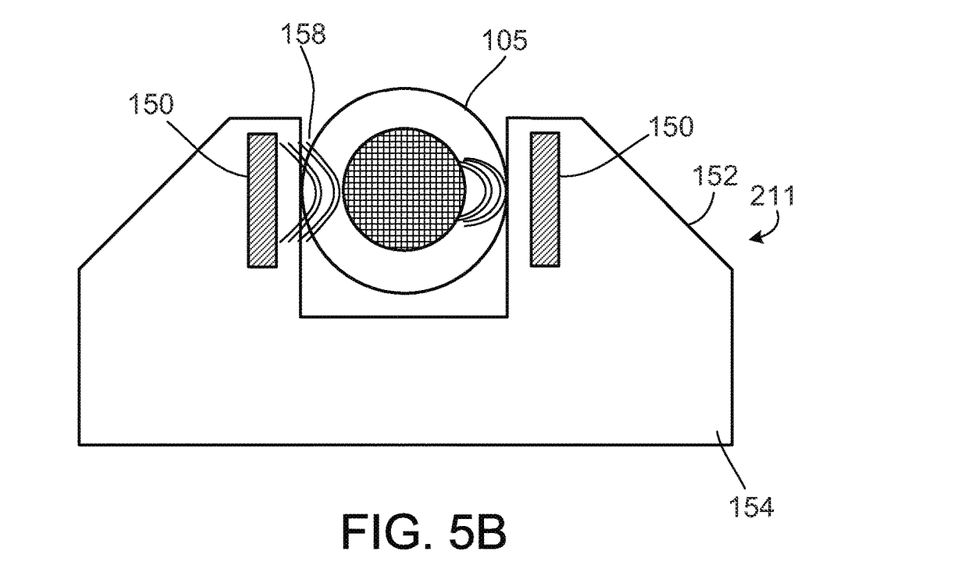

In some implementations, more than one magnetic sensor can be used in a magnetic sensor assembly, and the magnetic sensors can be placed in different configurations. Referring to FIGS. 5A and 5B, for example, a magnetic sensor assembly 211 includes two Hall effect sensors 150. The sensors 150 are contained in the tubing guides 152 on either side of the blood line 105. As shown in FIG. 5A, the blood line 105 contains no fluid and thus the magnetic field sensors 150 detect a magnetic field 158 at a default level. Referring to FIG. 5B, when a ferromagnetic fluid, such as Venofer® passes through the blood line 105, the magnetic field 158 is changed by the presence of the ferromagnetic fluid. The magnetic sensors 150 detect the change in the magnetic field 158 caused by the ferromagnetic fluid.

While the magnetic sensor assemblies 111, 211 have been described as having one or two magnetic sensors 150, the magnetic sensor assembly 111 can alternatively have more than two magnetic sensors 150.

With a magnetic sensor 150 that has the appropriate sensitivity, e.g., a sensitivity of at least 1 mV/gauss, it is believed that the magnetic sensor 150 can detect not only the presence of ferromagnetic fluid in the blood line 105 but also the quantity of ferromagnetic fluid in the blood line 105. For example, with a sensor of proper sensitivity, the sensor can output different voltages that precisely track the change in magnetic field detected. The magnetic field would change by different amounts corresponding to the amount of ferromagnetic fluid that passes through the magnetic field. The corresponding amounts of ferromagnetic fluid to output voltages can be recorded and stored as a lookup table accessible to the controller when the magnetic sensor is in use and providing different output voltages. The control unit can use this information to determine the amount of ferromagnetic fluid passing through the tube and verify the drug is being administered properly to the patient.

The control unit can also use the information from the magnetic sensor 150, along with information from other sensors, to determine the ratio of Venofer® to other fluids in the blood line 105. In some cases, for example, Venofer® can be mixed with saline to dilute the dosage of Venofer®, or Venofer® can be simultaneously delivered with other drugs. In such cases, the control unit can determine the amount of Venofer® in the blood line 105 based on the magnetic field detected by the sensor 150. In particular, the control unit can use the voltage received from the magnetic sensor to determine the quantity of Venofer® in the blood line, for example, by using a lookup table that lists quantities of Venofer® with corresponding voltages. Combined with information regarding the amount of saline in the blood line 105, the control unit can determine the strength of the dosage of the fluid in the blood line 105 to confirm the correct dosage is being administered. The information regarding the amount of saline in the blood line 105 can be provided, for example, by monitoring the pumps connected to the saline lines.

While the magnetic sensor 150 has been described to be a Hall effect magnetometer, other types of magnetic field sensors can be used.

Figure 6:
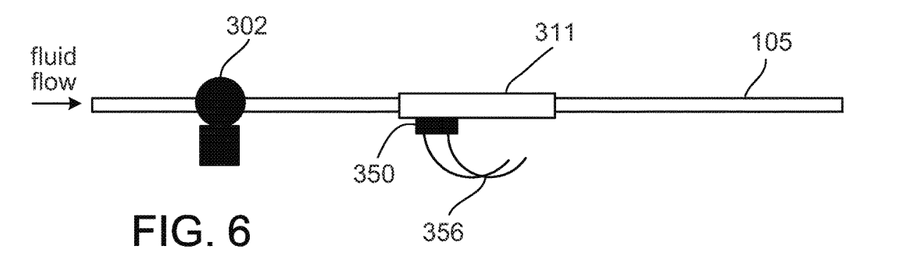
FIG. 6 is a schematic diagram of another magnetic sensor assembly.

In some implementations, the ferromagnetic fluid passing through the blood line 105 is magnetized before passing through the magnetic sensor assembly to allow the magnetic sensor assembly to more easily detect magnetic properties of the fluid. As shown in FIG. 6, for example, a magnet 302 is placed upstream of a magnetic sensor assembly 311. The magnet 302 is in a separate housing assembly that is releasably connected to the blood line 105. The magnetic sensor assembly 311 connects releasably to the blood line 105 downstream of the magnet 302 and includes a magnetic sensor 350. The magnetic sensor 350 is a transducer, such as a tape head, connected by wires 356 to a control unit. The magnetic sensor 350 is placed in close proximity to the magnet 302 (e.g., less than 0.2 inches). In some implementations, the thickness of the medical fluid tube can be reduced at the point of the transducer so that the transducer can more easily detect the magnetized ferromagnetic fluid passing through the medical fluid tube.

The magnet 302 aligns the particles in the ferromagnetic fluid as it passes by the magnet 302 and temporarily magnetizes the fluid. The magnetic sensor assembly 311 detects the magnetized ferromagnetic fluid passing through the tube. The magnetic sensor 350 converts the detected magnetic field into an electrical signal which it passes through the wires 356 to the control unit. The control unit interprets the electrical signal to determine whether a ferromagnetic fluid is present in the tube, and in some implementations, how much ferromagnetic fluid is present in the tube.

In some implementations, the magnet is contained in the housing of magnetic sensor assembly. In such implementations, the magnet and the magnetic sensor can be contained in separate compartments of the housing, configured to releasably hold the tube so that the magnet is upstream of the magnetic sensor.

Figure 7A:
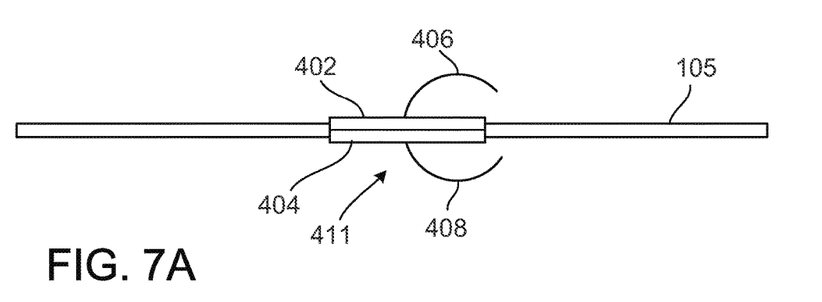
FIGS. 7A and 7B are schematic diagrams of another sensor assembly.
Figure 7B:
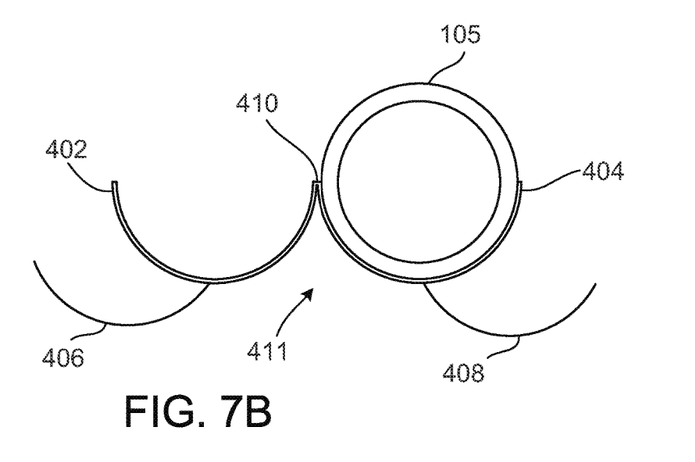

While the sensor assemblies described above detect magnetic fields of fluids to determine whether the fluid has ferromagnetic properties, other techniques can alternatively or additionally be used. As shown in FIGS. 7A and 7B, for example, a sensor assembly 411 includes two capacitance plates 402, 404. The capacitance plates 402, 404 are configured to hold the blood line 105 between the two plates 402, 404. More specifically, in the illustrated implementation, the capacitance plates 402, 404 are curved to conform to the shape of the blood line 105. Each capacitance plate 402, 404 is connected by a wire 406, 408 to a circuit.

The capacitance sensor assembly 411 uses capacitance measurement techniques to determine the presence of a ferromagnetic fluid or drug inside of the blood line 105. As the composition of the fluid changes, a sensed voltage that is proportional to the change in capacitance changes. Therefore, the sensor 411 can determine whether a fluid in the blood line 105 contains the ferromagnetic fluid. Each of these measurements can be made accurately, for example, at least on the order of the accuracy achieved by known gravimetric scales or pressure/volume measurements. The capacitance plates 402 and 404 can be disposed inside an insulative or dielectric housing.

Generally, the capacitance C between the two capacitor plates 402, 404 changes according to the function $C=k*(S/d)$, wherein k is the dielectric constant, S is the surface area of the individual plates, and d is the distance between the plates 402, 404. The capacitance between the plates 402, 404 changes proportionally according to the function $I/(R \times V)$, wherein R is a known resistance and V is the voltage measured across the capacitor plates 402, 404.

The dielectric constant k of, for example, Venofer®, is different than that of, for example, saline. Thus, if the blood line 105 contains Venofer®, the overall dielectric changes from one dielectric, saline, to a different dielectric, due to the increasing amount of Venofer® contained in the mixture of the fluid between the capacitance plates 402 and 404.

As the ferromagnetic fluid enters the mixture of the fluid in the blood line 105, the overall capacitance changes, i.e., increases or decreases, respectively. The capacitance sensor 411 generates a high impedance potential across the active and grounded capacitor plates 402 and 404, respectively. The high impedance potential is indicative of an amount of ferromagnetic fluid, such as Venofer®, in the blood line 105.

A capacitance sensing circuit (not illustrated) receives the signal through the wires 406, 408 and amplifies the high impedance signal to produce a low impedance potential. The amplified potential is converted to a digital signal and fed to the control unit, where it determines the presence or the amount of ferromagnetic fluid in the blood line 105.

In the illustrated implementation, the capacitance plates 402, 404 form a clamshell, connected by a hinge 410. Spherical, cubical, rectangular or other shapes are possible for the capacitance plates. In some implementations, the capacitance plates can be flat and configured to be a distance apart that is less than the diameter of the blood line. The blood line can thus be slightly compressed between the two plates.

In some implementations, the capacitance sensor assembly 411 can be placed in other locations on the hemodialysis system to be used to detect the presence of liquid in the tube versus air, or to detect the presence of air bubbles in a fluid.

Referring back to FIG. 1, while the sensor assemblies have been described as being placed on the blood line 105 downstream of the drip chamber 106, the sensor assemblies can alternatively or additionally be placed in other locations on the hemodialysis system 100. The sensor assemblies can, for example, be placed on the drug delivery line 104, upstream of the drip chamber 106. In certain implementations, the sensor assemblies can be placed on the blood line 105 downstream of the blood pump 108, between the blood pump 108 and the dialyzer 110. In certain implementations, multiple sensor assemblies can be used, placed in different locations on the hemodialysis system 100.

While the sensor assemblies have been described to send output signals to the control unit of the drug delivery device 103, the sensor assemblies can alternatively or additionally be configured to send output signals to a separate control unit. In some implementations, for example, the sensor assemblies are configured to send output signals to a control unit of the hemodialysis machine 101.

While the drug delivery devices above have been described as being used to deliver Venofer® and/or Epogen®, Venofer® can be delivered with any of various other types of "drugs," i.e., pharmaceuticals as well as other fluids delivered to a patient intravenously. Other drugs that are contemplated to be delivered to the patient along with the Venofer® include, but are not limited to, phosphate binders, vitamin D, and anticoagulants.

Additionally, while the sensor assemblies have been described as detecting Venofer®, they can be used to detect any of various other drugs containing ferromagnetic materials. Examples of such drugs include generic iron sucrose supplements and other medications intended to supplement iron deficiency.

Any of various types of drug delivery systems, including systems that include different types of vial holding/spiking assemblies and/or different fluid line sets than those described above can be used. Other examples of such systems are described in U.S. patent application Ser. No. 12/827,119, which is incorporated by reference herein.

While the drug delivery device 103 has been described as being connected to the user interface 134 of the hemodialysis machine 101, in certain implementations, the drug delivery device 103 is equipped with its own user interface.

While the sensor assemblies have been described to be used on a hemodialysis system 100, the sensor assemblies can be used as a component of any of various other types of medical devices or medical systems to detect the presence of ferromagnetic fluids in a tube. Examples include standalone drug delivery devices and systems and intravenous infusion systems that are only intended to infuse iron sucrose.

What is claimed is:

1. A dialysis system comprising:
   a dialysis machine;
   a blood line connected to the dialysis machine;
   a drug delivery device connected to the blood line via a drug delivery line to deliver a ferromagnetic medical fluid into the blood line; and
   a sensor assembly connected to the blood line at a location downstream of the connection to the drug delivery line, the sensor assembly comprising:
      a housing configured to releasably hold the blood line; and
      a sensor secured to the housing, the sensor configured to detect a change in strength of a magnetic field when the ferromagnetic medical fluid passes through the blood line and output a signal corresponding to the strength of the magnetic field;
   a data processing apparatus adapted to receive the signal from the sensor; and
   a computer storage medium encoded with a computer program, the program comprising instructions that when executed by the data processing apparatus cause the data processing apparatus to perform operations comprising:
      receiving information regarding desired flow rates of the ferromagnetic medical fluid and blood through the blood line;
      receiving information regarding a flow rate of the blood;
      receiving information regarding the detection of the change in strength of the magnetic field due to ferromagnetic properties of the ferromagnetic medical fluid when the ferromagnetic medical fluid passes through the blood line;
      calculating an amount of the ferromagnetic medical fluid passing through the blood line based on the received information; and
      determining whether actual flow rates of the ferromagnetic medical fluid and the blood are equal to the desired flow rates based on the flow rates and the detection of the change in magnetic field.

2. The dialysis system of claim 1, further comprising a drip chamber connected to the blood line, the drug delivery line connected to the blood line via the drip chamber, and the sensor assembly connected to the blood line downstream of the drip chamber.

3. The dialysis system of claim 1, further comprising a magnet adjacent the blood line, the magnet located upstream of the sensor assembly and configured to magnetize the ferromagnetic medical fluid that passes through the medical fluid tube.

4. The dialysis system of claim 3, wherein the magnet is located at a distance of 0.1 inches or less from the sensor assembly.

5. The dialysis system of claim 1, wherein the program comprises instructions that when executed by the data processing apparatus cause the data processing apparatus to perform operations comprising:
   determining whether the medical fluid is present in the blood line.

6. A medical fluid delivery method comprising:
   introducing a ferromagnetic medical fluid to blood in a blood line;
   detecting a magnetic field of the blood in the blood line at a location downstream of the introduction of the ferromagnetic medical fluid, where the magnetic field is due to ferromagnetic properties of the ferromagnetic medical fluid in the blood;
   receiving information regarding desired flow rates of the ferromagnetic medical fluid and the blood through the blood line;
   receiving information regarding a flow rate of the blood;
   based on the detection of the magnetic field, calculating an amount of the ferromagnetic medical fluid in the fluid passing through the medical fluid tube; and
   based on the flow rates and the detection of the magnetic field, determining whether actual flow rates of the ferromagnetic medical fluid and blood are equal to the desired flow rates.

7. The method of claim 6, the method further comprising magnetizing the ferromagnetic medical fluid in the blood line.

8. The method of claim 6, wherein the method is a computer-implemented method performed by a data processing apparatus.

* * * * *